United States Patent
Gutterson et al.

(10) Patent No.: US 6,521,458 B1
(45) Date of Patent: Feb. 18, 2003

(54) COMPOSITIONS AND METHODS FOR IMPROVED PLANT TRANSFORMATION

(75) Inventors: Neal Gutterson, Oakland, CA (US); William G. Hanson, Walnut Creek, CA (US)

(73) Assignee: DNA Plant Technology Corporation, Nogales, AZ (US)

(*) Notice: Subject to any disclaimer, the term of this patent is extended or adjusted under 35 U.S.C. 154(b) by 239 days.

(21) Appl. No.: 09/302,980

(22) Filed: Apr. 30, 1999

Related U.S. Application Data

(60) Provisional application No. 60/086,440, filed on May 22, 1998.

(51) Int. Cl.[7] .................. C12N 15/31; C12N 15/84; C12N 15/82; C12N 5/04; A01H 5/00
(52) U.S. Cl. .................. 435/469; 800/278; 800/294; 800/295; 435/69.1; 435/320.1; 435/419; 435/468; 435/480; 435/199; 435/91.4; 536/23.1; 536/23.2; 536/23.7; 536/24.1
(58) Field of Search .................. 800/278, 294, 800/295; 435/199, 69.1, 91.4, 419, 468, 469, 480, 320.1; 536/23.1, 23.7, 23.2, 24.1

(56) References Cited

FOREIGN PATENT DOCUMENTS

EP  0537 399  * 4/1993

OTHER PUBLICATIONS

McBride et al. Plant Molecular biology, vol. 14, pp. 269–276, 1990.*
Ramanathan et al. Plant Molecular Biology, vol. 28, pp. 1149–1154, 1990.*
Hartley, R. Journal of Molec. Biol. vol. 202, pp. 913–915, 1988.*
Evans et al. Biochem. Soc. Trans. 20: 344S, 1990.*
Kononov et al., *Plant J.,* 11:945–57, (1997).
Wenck et al., *Plant Mol. Biol.,* 34:913–22 (1997).
Martineau et al., *Plant Cell,* 6: 1032–33 (1994).
Ramanathan and Vehluthambi *Plant Mol. Biol.,* 28: 1149–54, 1995.
Megan et al., *Nature* 297:162–64 (1982).
Pavlovsky et al., *FEBS Lett.* 162:167–70 (1983).
Fujii et al., *Biosci. Biotechnol. Biochem.* 59:1869–1874 (1995).
Wallis et al., *Eur. J. Biochem* 220:447–54 (1994).
Newman et al., *Science* 269:656–63 (1995).
Eder et al., *J. Mol. Biol.* 233:293–304 (1993).

* cited by examiner

Primary Examiner—David T. Fox
Assistant Examiner—Medina A. Ibrahim

(57) ABSTRACT

The present invention provides methods for eliminating plants containing non-T-DNA sequences derived from a T-DNA vector. More specifically, the present invention provides a method for killing plant cells that receive non-T-DNA sequences based on incorporation of a lethal polynucleotide sequence into the non-T-DNA portion of the vector.

16 Claims, 10 Drawing Sheets

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:upper strand
      of octopine Ti plasmid right border (pTiA6, TL DNA) site that
      initiates T-DNA transfer

<400> SEQUENCE: 1
ggcaggatat ataccgttgt aatt                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:upper strand
      of octopine Ti plasmid left border (pTiA6, TL DNA) site that
      terminates T-DNA transfer

<400> SEQUENCE: 2
ggcaggatat attcaattgt aaat                                            24

<210> SEQ ID NO 3
<211> LENGTH: 525
<212> TYPE: DNA
<213> ORGANISM: Artificial Sequence
<220> FEATURE:
<223> OTHER INFORMATION: Description of Artificial Sequence:Barnase-INT
      sequence with insertion of IV2 intron of ST-LS1
      gene
<220> FEATURE:
<221> NAME/KEY: intron
<222> LOCATION: (180)..(368)
<223> OTHER INFORMATION: intron sequence in the Arg codon at position 59
      of the mature barnase protein

<400> SEQUENCE: 3
atggcacagg ttatcaacac gtttgacggg gttgcggatt atcttcagac atatcataag      60
ctacctgata attacattac aaaatcagaa gcacaagccc tcggctgggt ggcatcaaaa     120
gggaaccttg cagacgtcgc tccggggaaa agcatcggcg gagacatctt ctcgaacagg     180

-continued

```
taagtttctg cttctacctt tgatatatat ataataatta tcattaatta gtagtaatat      240
aatatttcaa atattttttt caaaataaaa gaatgtagta tatagcaatt gcttttctgt      300
agtttataag tgtgtatatt ttaatttata acttttctaa tatatgacca aaatttgttg      360
atgtgcaggg agggcaagct cccgggcaaa agcggacgaa catggcgtga agcggatatt      420
aactatacat caggcttcag aaattcagac cggattcttt actcaagcga ctggctgatt      480
tacaaaacaa cggaccatta tcagaccttt acaaaaatca gataa                     525
```

COMPOSITIONS AND METHODS FOR IMPROVED PLANT TRANSFORMATION

CROSS-REFERENCES TO RELATED APPLICATIONS

The present application claims priority to the U.S. provisional application No. 60/086,440, filed May 22, 1998.

FIELD OF THE INVENTION

This invention relates to plant genetic engineering. In particular, the invention is for the production of transformed plants in which only sequences between the right border and left border elements of Agrobacterium are obtained in selected plant cells.

BACKGROUND OF THE INVENTION.

Agrobacterium-mediated DNA delivery is a routine method for delivering DNA to plant cells for the purpose of producing genetically modified plants. Typically, these methods involve the use of disarmed Agrobacterium strains in which genes of interest are incorporated between right border and left border elements of a Ti plasmid. Work done in the late 1970s and early 1980s provided evidence that the sequences between the right border (RB) and left border (LB) were found in plant cells of tumor lines obtained following infection with wild isolates of *Agrobacterium tumefaciens* (Chilton et al., *Nature*, 275:147–49 (1978); Depicker et al., *Nature*, 275:150–53 (1978)). This sequence, commonly transferred to plant tumors, was taken to be the T-DNA, although it was known then that sequences in addition to this "common DNA" could be found in tumor cells (Thomashow et al., *Cell*, 19:729–39 (1980)).

The RB sequence has since been shown to function as a site for nucleolytic cleavage by virD2 protein, and initiation of replicative DNA transfer (Albright et al., *J. Bacteriol.* 169:1046–55 (1987), and Howard et al. DNAs 86:4017–21 (1989)). The LB element, with a sequence very similar to that of the RB, is the site of termination for transfer of sequences between the RB and LB. The LB element has also been shown to be a site for nucleolytic cleavage (Albright et al., *J. Bacteriol.* 169:1046–55(1987)). Albright et al. proposed that following cleavage at either border sequence, replication is initiated unidirectionally using a strand-displacement mechanism.

Based on this understanding of T-DNA transfer, plant molecular biologists engineered recombinant T-DNAs in which right and left border elements were placed around sequences they desired to transfer to plant cells. These recombinant T-DNA's have been used successfully for introducing the sequences between right and left border elements into plant cells. Schilperoort and his colleagues (see, e.g., U.S. Pat. No. 5,464,763) demonstrated that artificial T-DNAs could be constructed in a vector distinct from the Ti plasmid itself, which contained the functions necessary for transfer of T-DNA sequences into plant cells. Such T-DNA vectors have been used commonly by plant genetic engineers, in combination with disarmed Agrobacterium strains, for the transfer of engineered genes into plant cells.

Recently, a number of authors have reported the transfer of sequences other than those between right and left border elements into plant cells that have been selected for the presence of sequences that lie between the borders (Kononov et al., *Plant J.*, 11:945–57, (1997); Wenck et al., *Plant Mol. Biol.*, 34:913–22 (1997). A variable number of plant cells selected for transfer of sequences between the border elements also contain sequences beyond the left border. The frequency varies from 5% to over 75% (Martineau et al., *Plant Cell*, 6: 1032–33 (1994)). These sequences are thought to be transferred to the DNA either as a result of failure to terminate transfer at the left border, or by virtue of transfer initiated at the left border. In some examples of transgenic plants carrying sequences beyond the left border, the non-T-DNA sequences are integrated at locations distinct from ones carrying between border sequences.

It is often desirable to produce a population of transgenic plants that contain only those sequences bounded by the border elements. Although means for identifying such plant have been proposed (see, e.g., Ramanathan and Veluthambi *Plant Mol. Biol.*, 28: 1149–54, 1995), the art lacks simple and cost effective methods for producing a population of transgenic plants in which the number of transgenic individuals with non-T-DNA sequences is reduced substantially. The present invention provides these and other advantages.

SUMMARY OF THE INVENTION

The present invention provides methods for eliminating plants containing non-T-DNA sequences derived from a T-DNA vector. More specifically, the present invention provides a method for killing plant cells that receive non-T-DNA sequences derived from the T-DNA vector where the method is based on incorporation of a lethal polynucleotide sequence into the non-T-DNA portion of the vector.

The methods comprise introducing into plant cells a T-DNA vector comprising a T-DNA sequence having a right border, a left border and the polynucleotide of interest positioned between the right border and the left border. Also included in the vector is a non-T-DNA sequence comprising a lethal polynucleotide sequence. Plant cells are then selected which comprise the T-DNA sequence and do not comprise the lethal polynucleotide sequence. The plant cells are then regenerated into transgenic plants.

The lethal polynucleotide can encode a lethal polypeptide (e.g., a ribonuclease) or encode a lethal mRNA transcript (e.g., a ribozyme or antisense RNA). In some embodiments, the ribonuclease is Barnase. The lethal polynucleotide may be altered to prevent expression in the Agrobacterium host. This can be accomplished, for instance, by including an intron in the coding region. The non-T-DNA sequence may further comprise a screenable marker and the method may further comprise detection of the screenable marker in the plant cells. Exemplary screenable markers include β-glucuronidase.

The invention also provides vectors useful in the methods of the invention, as well as plant cells made by the methods.

DEFINITIONS

Figure 1:
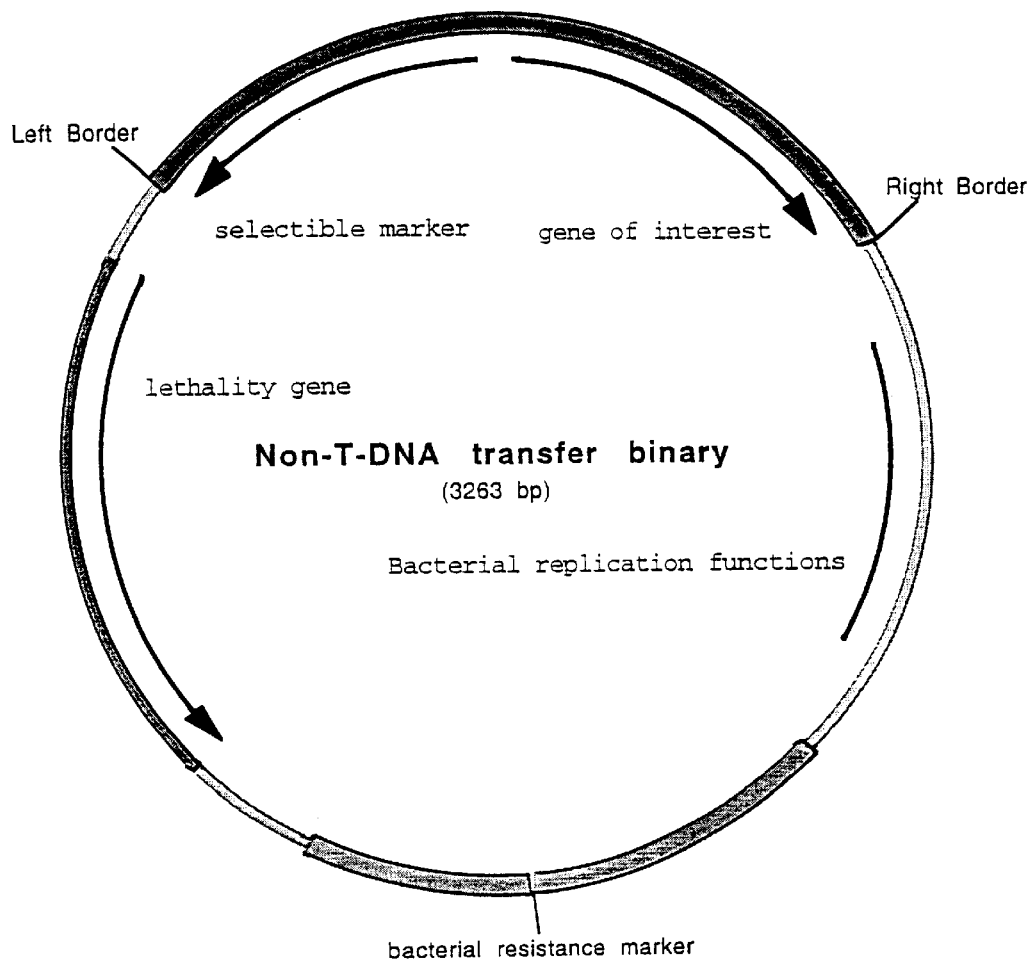
FIG. 1 shows a schematic map of a non-T-DNA transfer binary vector.
Figure 2A:
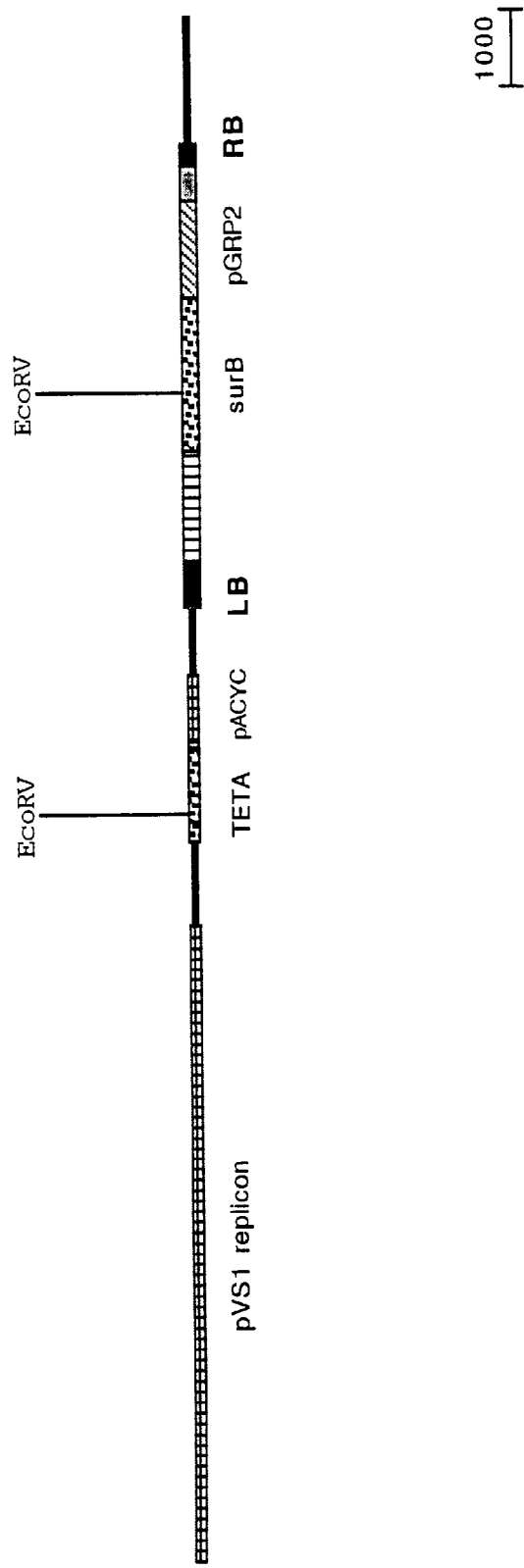
FIGS. 2A–I show restriction maps of various constructs used in the invention.
Figure 2B:
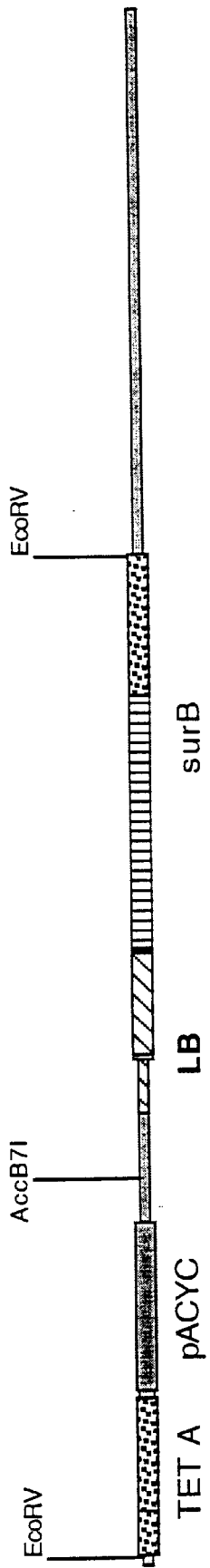
Figure 2C:
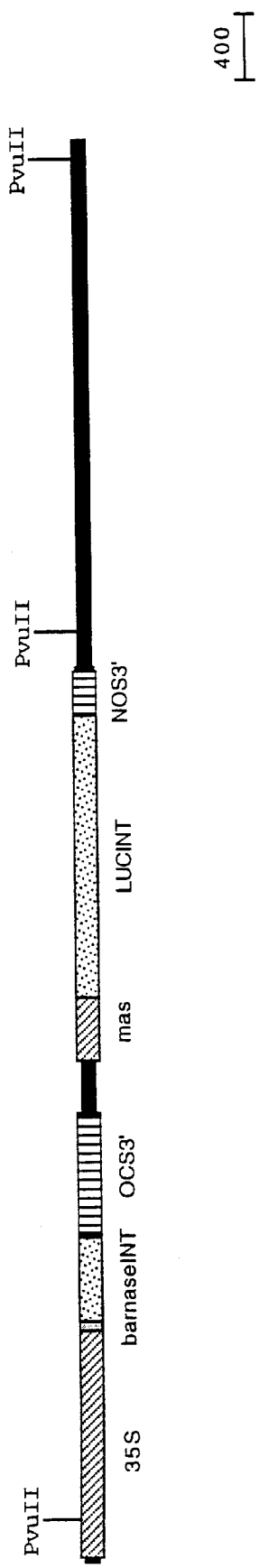
Figure 2D:
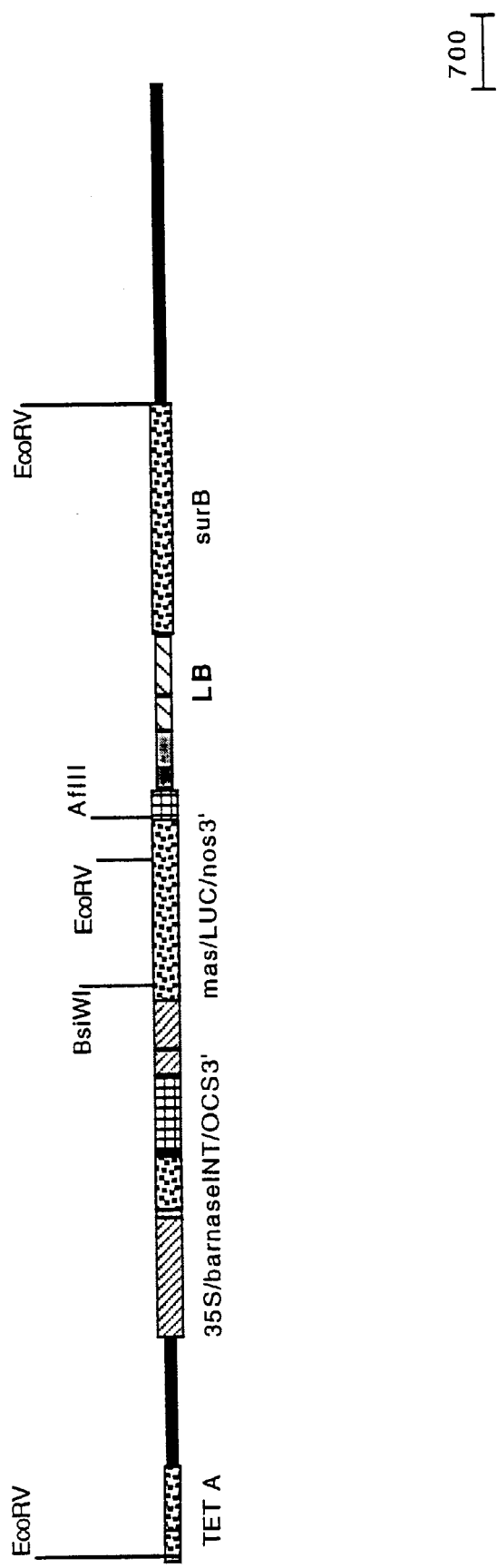
Figure 2E:
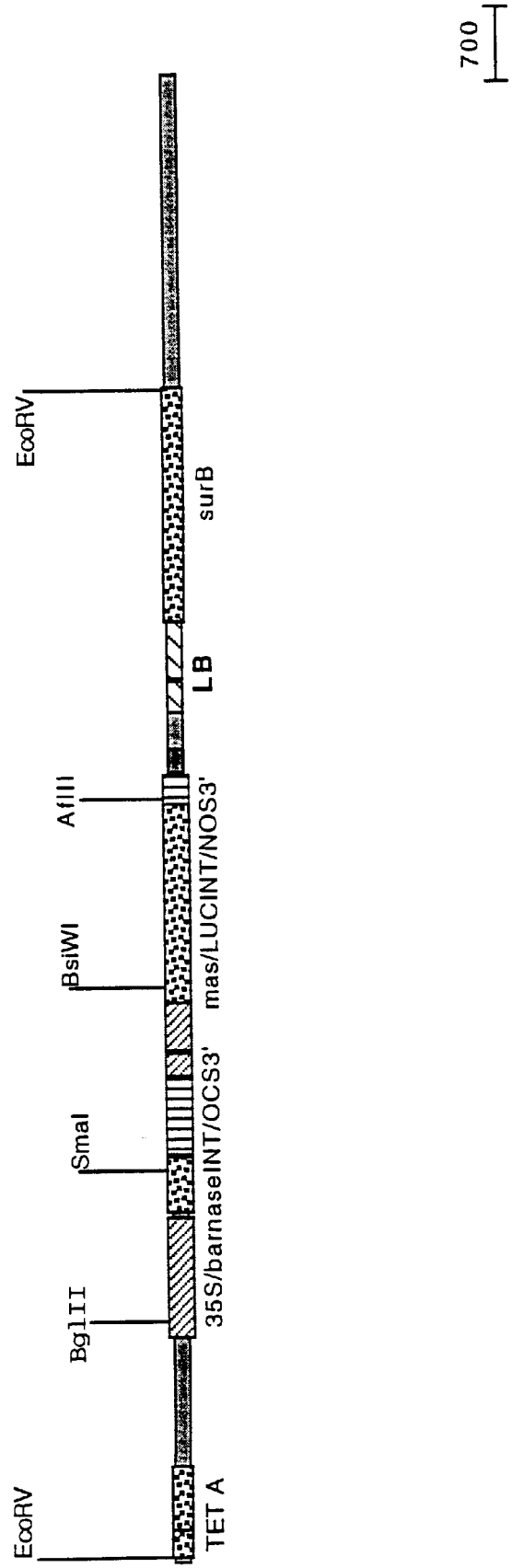
Figure 2F:
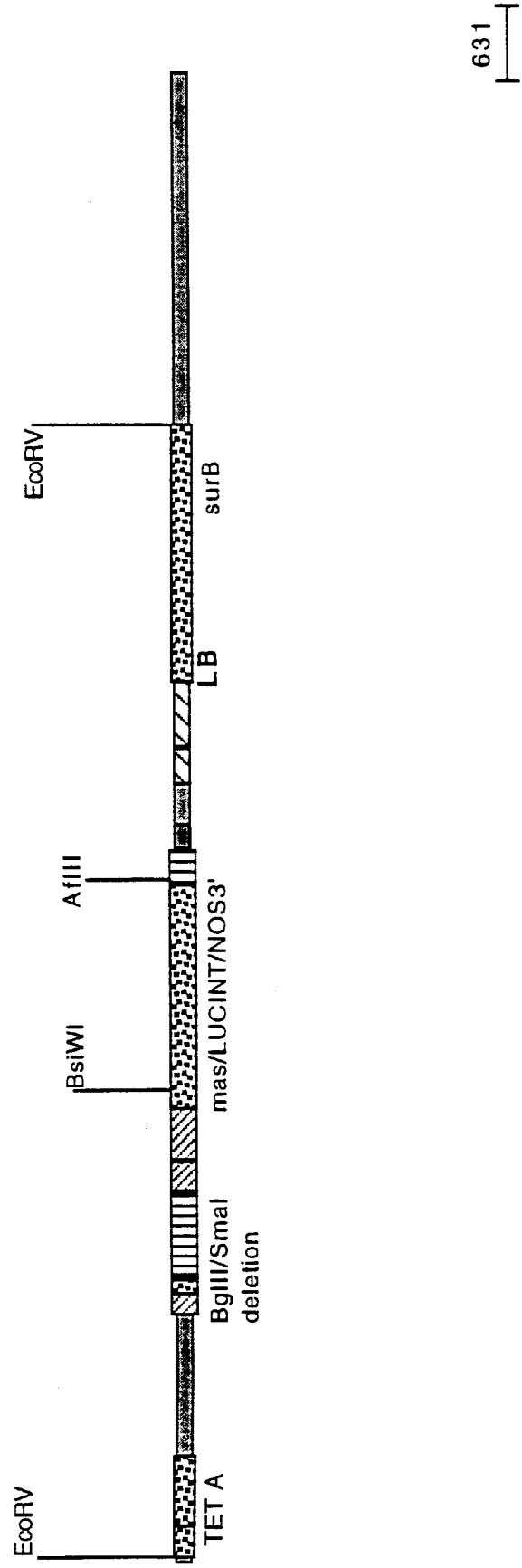
Figure 2G:
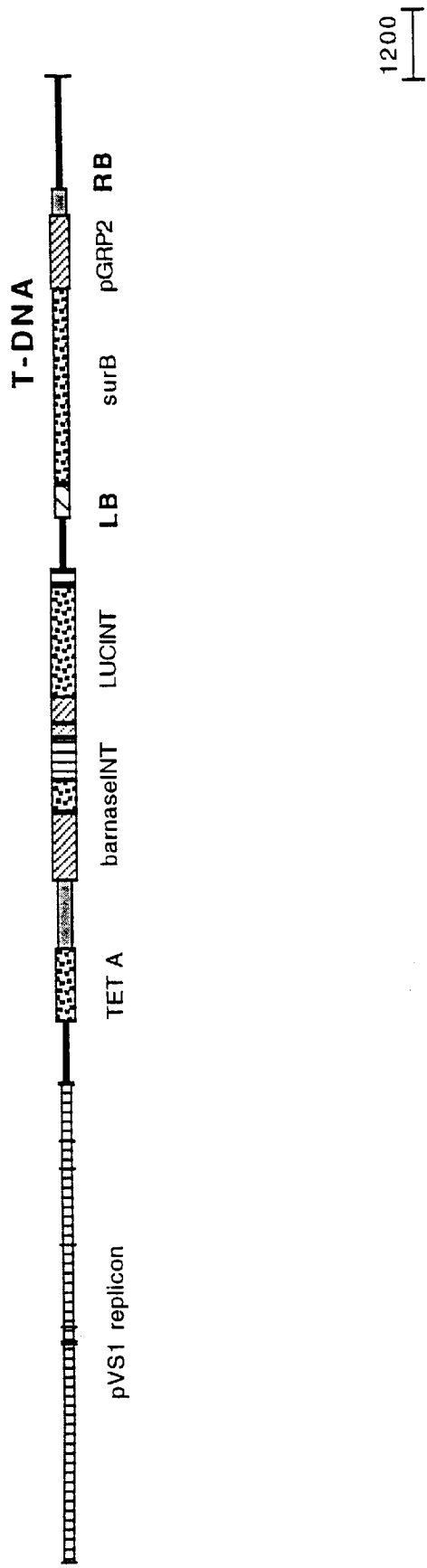
Figure 2H:
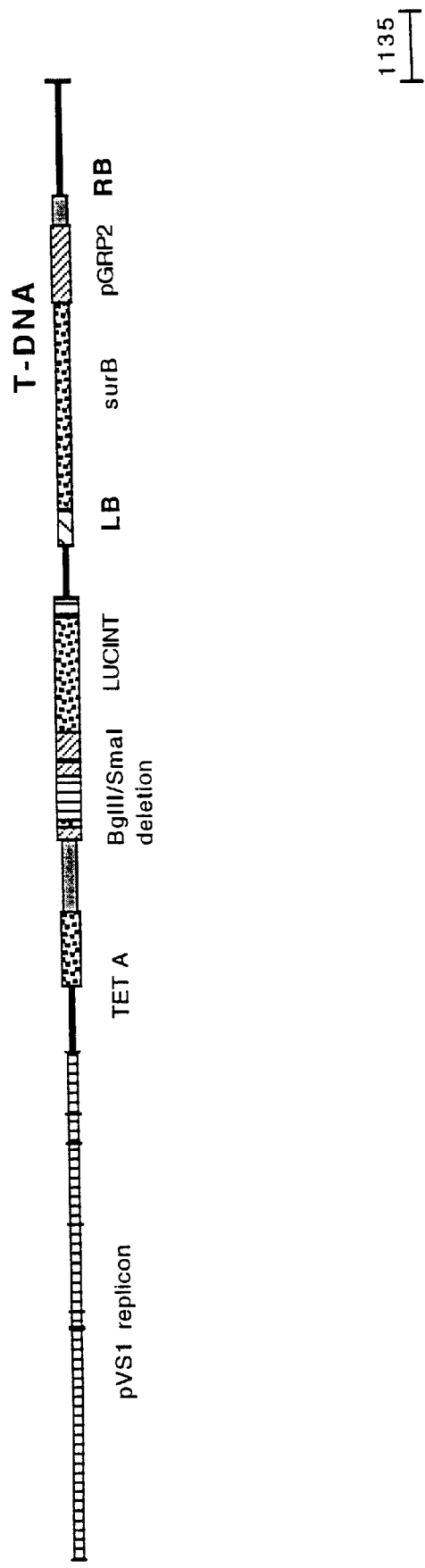
Figure 2I:
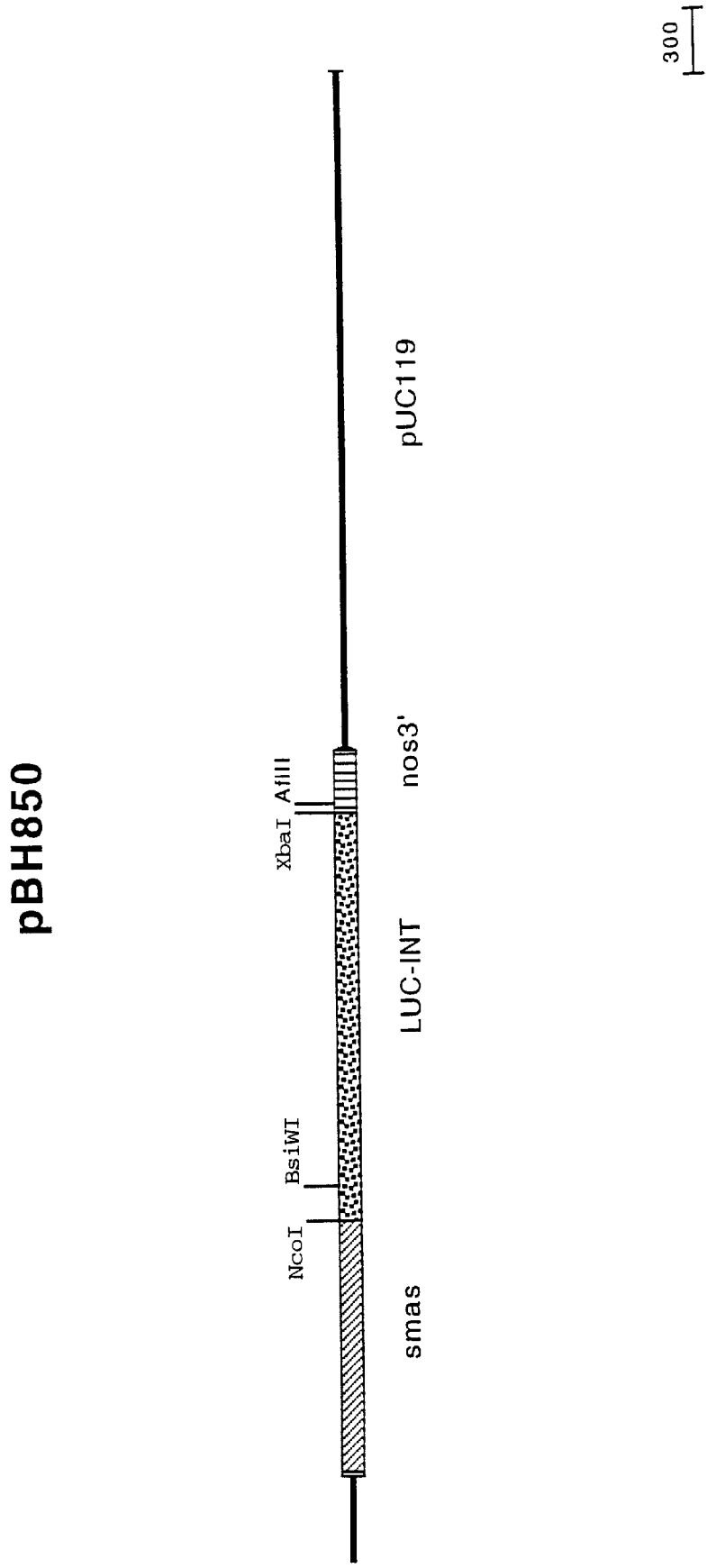

Units, prefixes, and symbols can be denoted in their SI accepted form. Numeric ranges are inclusive of the numbers defining the range. The headings provided herein are not limitations of the various aspects or embodiments of the invention which can be had by reference to the specification as a whole. Accordingly, the terms defined immediately below are more fully defined by reference to the specification in its entirety.

As used herein, the term "plant" includes reference to whole plants, plant organs (e.g., leaves, stems, roots, etc.), seeds and plant cells and progeny of same. The class of plants which can be used in the methods of the invention is generally as broad as the class of higher plants amenable to transformation techniques, including both monocotyledonous and dicotyledonous plants.

As used herein "operably linked" includes reference to a functional linkage between a promoter and a second sequence, wherein the promoter sequence initiates and mediates transcription of the DNA sequence corresponding to the RNA sequence which is typically transcribed into a polypeptide. Generally, operably linked means that the nucleic acid sequences being linked are contiguous and, where necessary to join two protein coding regions, contiguous and in the same reading frame.

As used herein, an "expression cassette" is a nucleic acid construct, generated recombinantly or synthetically, with a series of specified nucleic acid elements which permit transcription of a particular nucleic acid in a target cell. The expression cassette can be incorporated into a plasmid, chromosome, mitochondrial DNA, plastid DNA, virus, or nucleic acid fragment. Typically, the expression cassette portion of the expression vector includes, among other sequences, a nucleic acid to be transcribed, and a promoter.

As used herein, "right border" defines a 24 base pair DNA sequence that is found at the site that initiates T-DNA transfer. A typical sequence of the upper strand of an octopine Ti plasmid right border (pTiA6, TL DNA; Zambryski et al., *J. Mol. Appl. Genet.*, 1:361–70, (1982)) is:

5'-GGCAGGATATATACCGTTGTAATT-3' (SEQ ID NO:1)

Cleavage occurs between the C and the A at positions 3 and 4 in the bottom strand, and transfer is initiated replicatively in a 5' to 3' direction, with replicative displacement of the lower strand. Also included are sequences related to those found in the art as border sequences, and which are sites for virD2-endonucleolytic cleavage.

As used herein, "left border" defines a 24 base pair DNA sequence that is found at the site that terminates T-DNA transfer. A typical sequence of the upper strand of an octopine Ti plasmid left border (pTiA6, TL DNA; Zambryski et al., *J. Mol. Appl. Genet.*, 1:361–70 (1982)) is:

5'-GGCAGGATATATTCAATTGTAAAT-3' (SEQ ID NO:2)

Cleavage occurs between the C and the A at positions 3 and 4 in the bottom strand, and transfer initiated at a right border sequence is terminated as a result of the cleavage in the bottom strand (Albright et al., *J. Bact.* 169:1045–55 (1987)). Also included are sequences related to those found in the art as border sequences, and which are sites for virD2-endonucleolytic cleavage.

As user herein, a "T-DNA vector" includes reference to any vector that contains at least two T-DNA border elements and which can be used to transfer nucleic acid between the borders to the genome of a plant cell.

As used herein, "T-DNA" is the DNA fragment which is transferred to the plant cell from a T-DNA vector. The T-DNA is positioned 5' of a right border element and 3' of a left border element, in either native or recombinant DNA vectors. In a T-DNA vector, the indicated right border and left border elements are generally the only border elements in the vector. In some applications, a vector may contain 4 border elements, designed for the delivery of two different T-DNAs.

As used herein, "non-T-DNA" is any DNA other than the T-DNA in a T-DNA vector of the invention. In a T-DNA vector, such DNA is positioned 3' of a right border and 5' of a left border.

As used herein, "lethal" includes reference to a polynucleotide or polypeptide that is cytotoxic to an extent that it kills cells or inhibits cell division or differentiation. Thus, "lethal" includes reference either to 1) the disruption of a cell through perturbation of some function of the cell or by degradation of a component of the cell, or 2) to the prevention of continued growth of a cell through perturbation of some function of the cell or degradation of some component of the cell. By way of example, but not limitation, typical cellular functions in the context of the instant invention are protein synthesis, RNA synthesis, maintenance of osmotic competence, lipid synthesis, DNA synthesis. Typical cellular components subject to degradation in the context of the instant invention are proteins, carbohydrates, membranes, deoxyribonucleic acids, ribonucleic acids.

As used herein, "disarmed" includes reference to Ti plasmids in which genes capable of causing tumors upon transfer to plant cells, and located between T-DNA border elements, have been deleted.

As used herein, "heterologous" is a nucleic acid that originates from a foreign species, or, if from the same species, is substantially modified from its original form. For example, a promoter operably linked to a heterologous structural gene is from a species different from that from which the structural gene was derived, or, if from the same species, one or both are substantially modified from their original form. Thus, a "heterologous expression cassette" is one that comprises at least one element not endogenous to the species or sub-species in which it is introduced.

As used herein, "polynucleotide" and "nucleic acid" includes reference to both double stranded and single stranded DNA or RNA. The terms also refer to synthetically or recombinantly derived sequences essentially free of non-nucleic acid contamination. A polynucleotide can be a gene subsequence or a full length gene (cDNA or genomic). Unless specifically limited, the term encompasses nucleic acids containing known analogues of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, and mRNA encoded by a gene.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that initiate transcription only in certain tissues, such as leaves, roots, fruit, seeds, tapetal tissue, anthers, stigmas, or flowers. Such promoters are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, cell type specific, and inducible promoters constitute the class of "non-constitutive" promoters. A "constitutive" promoter is a promoter which is active under most environmental conditions.

DETAILED DESCRIPTION OF THE INVENTION

The present invention provides method for transformation of plants in which a lethal polynucleotide is incorporated in a T-DNA vector, outside the region between the right and left border elements. Transformation of plants can be accomplished using the vector comprising a selectable marker between the border elements, and selecting for plant cells or tissues able to grow in a selective medium, such as a suitable antibiotic or herbicidal chemical. Typically, the lethal polynucleotide will encode a lethal polypeptide which is effective in plant cells, either prior to or following integration into the plant genome, but not in Agrobacterium cells.

Depicted in FIG. 1 is a general representation of a T-DNA vector of the present invention. Typically, such vector will include left and right border elements which define a T-DNA sequence. Between these two elements, the desired polynucleotide sequence and a selectable marker gene are placed in any operation with respect to each other. T-DNA vector will also include a lethal polynucleotide located in the non-T-DNA portion of the vector. Additionally, the vector may have a screenable marker gene, usually located distal to the lethal gene with respect to the directionality of T-DNA transfer. Also included the vector are sequences commonly included in T-DNA vectors, such as sequences suitable for replication of the vector in Agrobacterium, and a selectable marker for maintenance of the plasmid in Agrobacterium cells. The various elements of the vectors of the invention are described in more detail below.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual,* Cold Spring Harbor Laboratory, Cold Spring Harbor, N.Y., (1989).

Polynucleotides of Interest

As noted above, the invention provides methods for introducing desired polynucleotides into plants. The particular polynucleotide of interest is not a critical aspect of the invention. The polynucleotide can, for instance, encode a polypeptide conferring a desired phenotype on plants, such as pathogen resistance, herbicide resistance, modified levels of desired metabolites, and the like.

Alternatively, the polynucleotide may encode mRNA transcripts which inhibit expression of an endogenous gene and provide a desired phenotype. Anti-sense RNA inhibition of gene expression has been shown; see, e.g., Sheehy et al., *Proc. Nat. Acad. Sci. USA* 85:8805–8809 (1988), and Hiatt et al., U.S. Pat. No. 4,801,340. For examples of the use of sense suppression to modulate expression of endogenous genes see, Napoli et al., *The Plant Cell* 2:279–289 (1990), and U.S. Pat. No. 5,034,323.

Catalytic RNA molecules or ribozymes can also be used to inhibit gene expression. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. A general design and use of target RNA-specific ribozymes is described in Haseloff et al. *Nature,* 334:585–591 (1988).

For antisense suppression or sense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective.

Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

As noted above, the T-DNA will typically comprise a marker gene which confers a selectable phenotype on plant cells. The marker gene can be used to identify those plant cells which have been transformed. The particular marker gene used is not a critical aspect of the invention. A number of genes are known. For example, the marker may encode biocide resistance, particularly antibiotic resistance, such as resistance to kanamycin, G418, bleomycin, hygromycin, or herbicide resistance, such as resistance to chlorosluforon or Basta.

Lethal Polynucleotides

The present invention can be practiced with a range of functions capable of exerting a lethal effect upon plant cells. Broadly, the lethal polynucleotides of the invention can either disrupt essential functions of plant cells, or they can degrade essential components of plant cells. By the action of such lethal functions, plant cells will either cease growth or be killed. The lethal polynucleotides are preferably active only in plant cells so that propagation of the vectors in prokaryotes ( e.g., Agrobacterium) is possible. This can be accomplished, for instance, by inserting a plant intron in the lethal polynucleotide. In plant cells the intron will be spliced out, thus allowing for expression of a lethal polypeptide. Alternatively, the promoter driving expression of the lethal polynuceotide can be selected to be active only in plant cells.

Typically, the lethal polynucleotides of the invention encode lethal polypeptides, which can include, but are not limited to proteases, ribonucleases such as Barnase, deoxyribonuclease, lipase, cell wall hydrolase. Exemplary polypeptides of the present invention include ribonucleases such as Barnase (Megan et al., *Nature* 297:162–64 (1982)), binase (Pavlovsky et al., *FEBS Lett.* 162:167–70 (1983)), Ribonuclease T1 (Fujii et al., *Biosci. Biotechnol. Biochem.* 59:1869–1874 (1995)), nucleases such as colicin E9 (Wallis et al., *Eur. J. Biochem* 220:447–54 (1994)) or BamHI (Newman et al., *Science* 269:656–63 (1995)), and proteases such as subtilisin BPN' (Eder et al., *J. Mol. Biol.* 233:293–304) or other members of the subtilisin family. Other polypeptides for creating cell toxicity or inhibition include those which produce toxic substances, disrupt cell function, suppress genes required by the cell, and disrupt mitochondrial function.

In addition to polypeptides, the transcription products of lethal polynucleotides can be used to suppress expression of endogenous plant genes and yield a lethal result. These include cassettes which provide sense or antisense suppression, or ribozymes which, in combination with a second expression cassette, inhibit or kill the cell. The use of sense suppression, antisense suppression and ribozymes is discussed above.

Generally, the position of the lethal polynucleotide in the non-T-DNA sequences of the vectors of the invention is not critical. As noted above, non-T-DNA sequences that are transferred are commonly from the region of the T-DNA vector just 5' to the left border. Thus, in some embodiments, the lethal polynucleotide is positioned proximal to the left border. Preferably, it positioned within about 10 kb, more preferably within about 5 kb, and most preferably within about 1 kb of the left border.

Promoters

The promoters employed in the instant invention as part of the expression cassettes of the invention (e.g., those comprising the lethal polynucleotides, the polynucleotides of interest, and the like) preferably function effectively in the target cells for Agrobacterium-mediated DNA delivery. The chosen promoters may function effectively in cells other than the target cells. One useful class of promoters are those generally characterized as constitutive. Examples of constitutive promoters include the cauliflower mosaic virus (CaMV) 35S transcription initiation region, the FMV 34S promoter, the 1'- or 2'-promoter derived from T-DNA of *Agrobacterium tumafaciens,* and other transcription initiation regions from various plant genes known to those of skill.

Alternatively, the plant promoter may direct expression of the operably linked nucleic acid in a specific tissue or may be otherwise under more precise environmental or developmental control. Examples of environmental conditions that may effect transcription by inducible promoters include anaerobic conditions, elevated temperature, or the presence of light. Such promoters are referred to here as "inducible" or "tissue-specific" promoters. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

Examples of promoters under developmental control include promoters that initiate transcription only (or primarily only) in certain tissues, such as fruit, seeds, or flowers.

Other useful promoters are those that are effective in callus tissues, as such are often derived during plant transformation procedures. Other types of promoters can be selected for their activity in embryogenic tissue, where such tissues are being used as the explant for transformation. The CaMV 35S promoter is a preferred promoter for use with the present invention as it is active in all tissue types, so that a single vector can be used with any plant explant and transformation type.

Screenable Markers

In some embodiments, in combination with a lethal gene located in the non-T-DNA region, a screenable marker can be also be used. The screenable marker can be used as a final check, should a defective copy of the lethal gene be transferred. Since transfer moves from the left border in a direction away from the right border in T-DNA vectors, the screenable marker can be placed distal to the lethal gene with respect to the LB and the T-DNA. Suitable screenable markers are well known to those of skill in the art and include, for instance, β-glucuronidase (GUS), (Jefferson et al., *EMBO J.* 6:3901–3907 (1987)), firefly luciferase (LUC), (De Wet et al., *Mol. Cell. Biol.* 7:725–37 (1987)) or green fluorescent protein.

Transformation

The present invention can be practiced with a range of transformation methods, including any of the methods within the broad classes of organogenic and embryogenic regeneration methods. Organogenic methods are those in which shoots are derived either directly from a standard plant tissue explant, or from callus tissue that arises from a standard plant tissue explant during the transformation process, and then whole plants are derived from those shoots. Embryogenic methods are those in which specific tissue types capable of producing embryos are transformed, and then embryos are regenerated.

The T-DNA vectors of the present invention are DNA or RNA constructs which can be cloned and/or synthesized by any number of standard techniques. Expression cassette within the vectors (e.g., those encoding a desired polypeptide, the lethal polypeptide, and the like) will typically comprise transcriptional and translational initiation regulatory sequences which will direct the transcription of the polynucleotide encoding the polypeptide in the intended tissues of the transformed plant. The T-DNA vectors are introduced into the genome of the desired plant host using a conventional *Agrobacterium tumefaciens* host. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch et al. *Science,* 233:496–498 (1984), and Fraley et al. *Proc. Natl. Acad. Sci. USA* 80:4803 (1983).

The transformation techniques can be used with any plant to which Agrobacterium species can transfer DNA. This includes dicotyledonous and monocotyledonous plants, as it has been demonstrated recently that many monocots can be transformed by Agrobacterium. For instance, Agrobacterium transformation of rice is described by Hiei et al, *Plant J.* 6:271–282 (1994).

Suitable plant genera that can be used with the present invention include, for instance, Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum and Datura.

The present invention can be practiced with any explant for which transformation is possible. This includes, but is not limited to, leaf discs, stem explants, floral tissues, root tissue, embryogenic tissues, callus tissues, protoplasts, or suspension cells.

EXAMPLES

Example 1

This example describes the construction of 1) the binary vector containing barnase-INT and LUC-INT outside the left border, and 2) a control vector with a non-functional barnase-INT gene.

In order to test the efficacy of a lethal screen to prevent transfer of sequences past the left border, an existing binary vector was modified by placing a lethal gene and/or a visible marker gene outside of the T-DNA, just beyond the left border. In order to simplify the modification of the large (20 Kbp) binary vector pNG5185, the fragment to be modified was subcloned. This was accomplished by digesting pNG5185 with EcoRV, gel purifying the 5.4 Kbp fragment and ligating it into the EcoRV site of pGEM5Z (Promega) resulting in pAR4661. This EcoRV fragment contains a portion of the surB gene which is within the T-DNA borders, the left border sequence, the pACYC origin of replication and a portion of the TETA gene.

The luciferase gene was chosen as a visible marker gene and the barnase gene as a lethal marker gene. Since barnase is lethal in bacteria as well as plant cells, the barnase gene was modified by inserting a plant intron in its coding sequence. This was accomplished using recombinant PCR techniques as described by Higuchi (PCR Protocols, A Guide to Methods and Applications, Chapter 22 and references cited therein). SEQ ID NO:3 provides the barnase sequence and the position of insertion of the IV2 intron of the ST-LS1 gene (Rocha-Sosa et al., 1990).

In order to fuse the visible marker gene (LUC) and the lethal gene (barnase-INT), a fragment carrying both the 35S/barnase-INT/OCS3' and the mas/LUC/NOS3' chimeric genes was prepared. The following three digests were done:

pGEM11Zf(+/−) (Promega) with EcoRI/NotI and the 3.2 Kbp fragment was gel purified.

pAR4401 with EcoRI/HindIII and the 2.7 Kbp barnase-INT fragment was gel purified.

pLVC340 with NotI/HindIII and the 2.9 Kbp LUC fragment was gel purified.

These three fragments were ligated together using T4 DNA ligase giving rise to pBH500 which includes the mas promoter driving LUC with a NOS3' terminator and the 35S promoter driving barnase-INT with an OCS3' terminator in the cloning vector pGEM11Zf (Promega).

In order to place this fragment containing both the visible marker gene and the lethal marker gene outside the left border pBH500 was digested with PvuII and the 5.3 Kbp fragment was gel purified and cloned into the unique AccB7I site (filled in with T4 polymerase) of pAR4661 giving rise to pBH600. The final step involved the replacement of the EcoRV fragment of pNG5185 with the corresponding fragment of pBH600. The IV2 intron was inserted into the coding sequence of the LUC gene. The point of insertion was near the EcoRV site which allowed the introduction of a silent mutation, destroying the EcoRV site. The product of the PCR reaction was cloned as a blunt fragment into the SmaI site of the cloning vector Bluescript SK+ (Stratagene) using T4 DNA ligase and giving rise to pBH800.

Next, the plasmid pBH800 was digested with NcoI/XbaI and the 1.7 Kbp fragment (insert) was gel purified using a GenElute spin column (Supelco). The plasmid pLVC340 (smas/LUC) was digested with NcoI/XbaI and the 5.1 Kbp fragment (vector) was gel purified by the same method. Vector and insert were ligated using T4 DNA ligase, giving rise to pBH850 in which the LUC-INT gene is under the control of the smas promoter. The function of the resulting smas/LUC-INT chimeric gene was verified by introduction into pepper leaf discs via biolistics and subsequent luciferase assay.

The plasmid pBH850 was digested with AflII (which cuts in the NOS 3' terminator, 3' of the IV2 intron) and BsiWI (which cuts in the LUC-INT coding sequence, 5' of the IV2 intron). The 1.8 Kbp fragment (insert) was gel purified as described above. pBH600 was digested with the same pair of enzymes and the 13.8 Kbp fragment (vector) was gel purified. The vector and insert were ligated using T4 DNA ligase resulting in pBH660.

To replace the EcoRV fragment of pNG5185 with the modified EcoRV fragment of pBH660 the following EcoRV fragments were get purified: a 14.5 kbp fragment of pNG5185 and an 11 kbp fragment of pBH660. The fragments were mixed and ligated using T4 DNA ligase, giving rise to pBH700, which has functional barnase-INT and LUC-INT genes outside the left border.

To produce a non-functional barnase-INT control derivative of pNG5185, pBH660 was digested with BglII/SmaI, filled in with T4 polymerase and the 12.6 Kbp fragment was gel purified. This vector was religated resulting in pBH670 which is equivalent to pBH660 except that it has a 1.4 Kbp deletion of the 35S/barnase-INT gene fusion (non-functional barnase-INT). The 9.6 kbp EcoRV fragment of pBH670 containing the non-functional barnase-INT and functional LUC-INT genes was used in a reaction as described above for pBH660 to replace the original EcoRV fragment of pNG5185. The resulting plasmid was designated pBH710 (non-functional barnase-INT, functional LUC-INT).

Example 2

This example describes Agrobacterium-mediated transformation of tobacco using a lethal gene outside the left border.

The source of the explants was in vitro grown tobacco plants (cv Petite Havana) cultured on TCMA medium (½ MS salts, B5 vitamins, 100 mg/l m-inositol, 600 mg/l MES, 20 g/l sucrose, pH 5.6 and solidified with 7 g/l TC agar) at 27□C in 16 hr light. After removing the midrib, leaves were cut into explants ca. 2×2 mm. Explants were floated on minAsuc medium containing an overnight culture of LBA4404 cells diluted to 5×10$^7$ cells/ml and containing one of the binaries; pNG5185, pBH700 or pBH710. After several minutes explants were transferred to plates containing TCMA basal medium supplemented with the following; 0.5 mg/l BAP, 2 mg/lIAA and 100 µM acetosyringone. Explants were cocultivated on this medium, overlayed with filter paper discs, at 24° C./dark for two days. Explants were then transferred to TCMA basal medium supplemented with the following; 0.5 mg/l BAP, 2 mg/lIAA, 25 µg/l chlorsulfuron and 250 mg/l carbenecillin. The explants were cultured under the same conditions as the in vitro shoots and after 3 weeks shoots had formed on most of the explants. The transformation efficiency (transformed shoots/explants on selection) was determined for each of the three treatments and the shoots were transferred to TCMA basal medium supplemented with the following; 25 µg/l chlorsulfuron and 250 mg/l carbenecillin under the same culture conditions.

TABLE 1

Relative Transformation Efficiency

|  | pNG5185 | pBH700 | pBH710 |
|---|---|---|---|
| # transformed shoots | 184 | 88 | 156 |
| # explants selected | 48 | 63 | 76 |
| transformants/explant | 3.8 | 1.4 | 2 | pNG5185 = unmodified binary
pBH700 = active barnase-INT
pBH710 = barnase-INT deletion One week later a subset of transformants from each treatment was assayed for luciferase activity by removing a ca. 1×1 mm leaf explant and extracting total protein by grinding in 100 µl Cell Culture Lysis Reagent (25 mM Tris-phosphate (pH 7.8), 2 mM DTT, 2 mM 1,2-diaminocyclohexane-N,N,N',N'-tetraacetic acid, 10% glycerol and 1% triton X-100). Five µl of extract were mixed with 20 µl of substrate and the reaction read immediately in a scintillation counter (Beckman LS 6800), background reading is 30K–35K CPM. Values inputted below were after subtracting background. Readings of 50,000,000 CPM were the maximum detected by the scintillation counter.

TABLE 2

Luciferase Activity

| transformant | ×1000 CPM | transformant | ×1000 CPM | transformant | ×1000 CPM | transformant | ×1000 CPM |
|---|---|---|---|---|---|---|---|
| 700-01 | 13 | 700-38 | 11 | 710-01 | 50000 | 710-74 | 50000 |
| 700-05 | 3 | 700-40 | 15 | 710-07 | 8428 | 710-76 | 50000 |
| 700-07 | 3 | 700-41 | 6 | 710-09 | 32466 | 710-80 | 50000 |
| 700-08 | 4 | 700-42 | 6 | 710-10 | 2181 | 710-82 | 253 |
| 700-09 | 6 | 700-43 | 9 | 710-12 | 50000 | 710-83 | 92 |
| 700-10 | 5 | 700-46 | 10 | 710-15 | 677 | 710-84 | 50000 |
| 700-12 | 6 | 700-48 | 8 | 710-17 | 163 | 710-85 | 50000 |
| 700-13 | 11 | 700-49 | 9 | 710-18 | 50000 | 710-86 | 50000 |
| 700-16 | 5 | 700-50 | 6 | 710-20 | 50000 | 710-90 | 7596 |
| 700-17 | 6 | 700-51 | 15 | 710-22 | 50000 | 710-92 | 50000 |
| 700-18 | 8 | 700-52 | 10 | 710-23 | 21957 | 710-96 | 50000 |
| 700-20 | 8 | 700-54 | 7 | 710-34 | 50000 | 710-97 | 50000 |
| 700-22 | 10 | 700-57 | 6 | 710-37 | 753 | 719-99 | 50000 |
| 700-23 | 7 | 700-58 | 11 | 710-39 | 50000 | 710-101 | 50000 |
| 700-24 | 45 | 700-65 | 77 | 710-40 | 150 | 710-103 | 8 |
| 700-26 | 6 | 700-66 | 6 | 710-44 | 51 | 710-106 | 50000 |
| 700-27 | 9 | 700-68 | 10 | 710-46 | 50000 | 710-108 | 259 |
| 700-29 | 50000 | 700-69 | 10 | 710-56 | 31221 | 710-112 | 50000 |
| 700-30 | 28 | 700-70 | 7 | 710-57 | 50000 | 710-113 | 50000 |
| 700-31 | 19 | 700-71 | 6 | 710-58 | 37 | 710-114 | 2856 |
| 700-32 | 2 | 700-73 | 10 | 710-68 | 1 | 710-117 | 50000 |
| 700-33 | 6 | 700-75 | 9 | 710-69 | 5 | 710-118 | 1254 |
| 700-34 | 9 | 700-77 | 14 | 710-71 | 0 | 710-119 | 505 |
| 700-35 | 8 | 700-79 | 6 | 710-72 | 50000 | 710-121 | 50000 |
| 700-36 | 28 | 700-82 | 35 | 710-73 | 47 | 710-122 | 5072 |

≧100000 CPM = positive

For these purposes, given that background readings were about 30K CPM, values greater than or equal to 100,000 CPM were taken as positive for the presence of LUC. The data presented in Table 2 indicates that the functional barnase-INT greatly reduced the incidence of transfer of sequences beyond the left border reflected in the low percentage (2%) of LUC+ transformants. The data also indicate the high incidence of beyond the border transfer in the control population (84% LUC+).

The data in Table 1 show the nominal impact that the barnase-INT construct had on the efficiency of transformation. Compared with the control binary (pBH710) the binary with the functional barnase-INT outside the T-DNA (pBH700) had only a 30% reduction in transformation efficiency. Comparing this binary with the non-modified binary (pNG5185), the reduction was less than three fold.

Example 3

This example describes tobacco transformation results demonstrating that barnase function is directly responsible for the reduction in DNA outside the T-DNA being present in transformned plants.

Transformations described in this example were performed essentially as described in example 2, with the following exceptions: The concentration of the bacterial inoculum was 2.5×107 cells/ml, explants were cocultivated for 4 days and in addition to wild type tobacco (WT) a barstar expressing line was also included (basrstar5). The barstar gene encodes a small polypeptide which inactivates the barnase enzyme by binding at an allosteric site. This binding can result in protection of a cell from the otherwise lethal effects of the barnase enzyme if an excess of barstar over barnase is produced. Barstar5 was included in the experiment to determine whether this line would provide sufficient protection to allow transfer of the barnase gene without lethality. This would result in a higher incidence of LUC positive plants in the barstar5 population compared with wild type after transformation with the pBH700 binary. After four weeks the transformation efficiency for the various treatments was determined (Table 3).

TABLE 3

Relative Transformation Efficiency

|  | 700/WT | 710/WT | 700/barstar5 | 710/barstar5 |
|---|---|---|---|---|
| # transformed shoots | 278 | 175 | 167 | 115 |
| # explants | 84 | 57 | 42 | 35 |
| transformants/explant | 3.3 | 3.1 | 4 | 3.3 | pBH700 = active barnase-INT
pBH710 = barnase-INT deletion

During the determination of transformation efficiency a subset of the shoots were assayed for LUC activity as described in example 2. The data in Table 4 presents the comparison of pBH700 (active barnase) and pBH710 (inactive barnase) in wild type tobacco.

TABLE 4

Luciferase Activity in WT Tobacco

| transformant | × 1000 CPM | transformant | × 1000 CPM |
|---|---|---|---|
| 700WT-1 | 4 | 710WT-1 | 17 |
| 700WT-2 | 6 | 710WT-2 | 156 |
| 700WT-3 | 141 | 710WT-3 | 50000 |
| 700WT-4 | 7 | 710WT-4 | 517 |
| 700WT-5 | 10 | 710WT-5 | 50000 |
| 700WT-6 | 9 | 710WT-6 | 50000 |
| 700WT-7 | 12 | 710WT-7 | 4133 |
| 700WT-8 | 13 | 710WT-8 | 2 |
| 700WT-9 | 266 | 710WT-9 | 157 |
| 700WT-10 | 27 | 710WT-10 | 50000 |
| 700WT-11 | 106 | 710WT-11 | 171 |
| 700WT-12 | 24 | 710WT-12 | 762 |
| 700WT-13 | 90 | 710WT-13 | 1974 |
| 700WT-14 | 191 | 710WT-14 | 240 |
| 700WT-15 | 41 | 710WT-15 | 5340 |
| 700WT-16 | 10 | 710WT-16 | 506 |
| 700WT-17 | 11 | 710WT-17 | 15 |
| 700WT-18 | 15 | 710WT-18 | 18038 |
| 700WT-19 | 31 | 710WT-19 | 301 |
| 700WT-20 | 6 | 710WT-20 | 50000 |
| 700WT-21 | 5 | 710WT-21 | 50000 |
| 700WT-22 | 101 | 710WT-22 | 17854 |
| 700WT-23 | 5 | 710WT-23 | 34132 |
| 700WT-24 | 22 | 710WT-24 | 16 |
| 700WT-25 | 31 | 710WT-25 | 7 |
| 700WT-26 | 10 | 710WT-26 | 50000 |
| 700WT-27 | 15 | 710WT-27 | 50000 |
| 700WT-28 | 61 | 710WT-28 | 2794 |
| 700WT-29 | 27 | 710WT-29 | 15356 |
| 700WT-30 | 36 | 710WT-30 | 6 |
| 700WT-31 | 54 | 710WT-31 | 50000 |
| 700WT-32 | 222 | 710WT-32 | 1568 |
| 700WT-33 | 9 | 710WT-33 | 535 |
| 700WT-34 | 30 | 710WT-34 | 141 |
| 700WT-35 | 0 | 710WT-35 | 50000 |
| 700WT-36 | 28 | 710WT-36 | 101 |
| 700WT-37 | 4 | 710WT-37 | 99 |
| 700WT-38 | 2 | 710WT-38 | 67 |
| 700WT-39 | 5 | 710WT-39 | 141 |
| 700WT-40 | 3 | 710WT-40 | 8951 |

≧100000 CPM = positive

The data presented in Table 4 is comparable to the luciferase data presented in Example 2. Although there is a higher percentage of LUC positive plants in the 700WT population in this example compared with example 2 (15% vs 2%) the relative difference between 700WT and 710WT populations is still highly significant (15% vs 80%).

Table 5 shows the comparison of the pBH700 binary transformed into both wild type and the barstarS tobacco line.

TABLE 5

Luciferase Activity of pBH700 Containing Plants in WT vs Barstar5

| transformant | × 1000 CPM | transformant | × 1000 CPM |
|---|---|---|---|
| 700WT-1 | 4 | 700B5-01 | 7 |
| 700WT-2 | 6 | 700B5-2 | 14 |
| 700WT-3 | 141 | 700B5-3 | 35306 |
| 700WT-4 | 7 | 700B5-4 | 48 |
| 700WT-5 | 10 | 700B5-5 | 50000 |
| 700WT-6 | 9 | 700B5-6 | 168 |
| 700WT-7 | 12 | 700B5-7 | 9046 |
| 700WT-8 | 13 | 700B5-8 | 19 |
| 700WT-9 | 266 | 700B5-9 | 50000 |
| 700WT-10 | 27 | 700B5-10 | 130 |
| 700WT-11 | 106 | 700B5-11 | 97 |
| 700WT-12 | 24 | 700B5-12 | 684 |
| 700WT-13 | 90 | 700B5-13 | 46 |
| 700WT-14 | 191 | 700B5-14 | 41 |
| 700WT-15 | 41 | 700B5-15 | 50000 |
| 700WT-16 | 10 | 700B5-16 | 169 |
| 700WT-17 | 11 | 700B5-17 | 43057 |
| 700WT-18 | 15 | 700B5-18 | 13 |
| 700WT-19 | 31 | 700B5-19 | 112 |
| 700WT-20 | 6 | 700B5-20 | 50000 |
| 700WT-21 | 5 | 700B5-21 | 81 |
| 700WT-22 | 101 | 700B5-22 | 93 |
| 700WT-23 | 5 | 700B5-23 | 4 |
| 700WT-24 | 22 | 700B5-24 | 275 |
| 700WT-25 | 31 | 700B5-25 | 262 |
| 700WT-26 | 10 | 700B5-26 | 139 |
| 700WT-27 | 15 | 700B5-27 | 199 |
| 700WT-28 | 61 | 700B5-28 | 50000 |
| 700WT-29 | 27 | 700B5-29 | 50000 |
| 700WT-30 | 36 | 700B5-30 | 509 |
| 700WT-31 | 54 | 700B5-31 | 14 |

TABLE 5-continued

Luciferase Activity of pBH700 Containing Plants in WT vs Barstar5

| transformant | × 1000 CPM | transformant | × 1000 CPM |
|---|---|---|---|
| 700WT-32 | 222 | 700B5-32 | 16 |
| 700WT-33 | 9 | 700B5-33 | 1895 |
| 700WT-34 | 30 | 700B5-34 | 28004 |
| 700WT-35 | 0 | 700B5-35 | 19 |
| 700WT-36 | 28 | 700B5-36 | 427 |
| 700WT-37 | 4 | 700B5-37 | 9 |
| 700WT-38 | 2 | 700B5-38 | 14 |
| 700WT-39 | 5 | 700B5-39 | 20 |
| 700WT-40 | 3 | 700B5-40 | 22 |
|  |  | 700B5-41 | 19 |
|  |  | 700B5-42 | 50 |
|  |  | 700B5-43 | 38 |
|  |  | 700B5-44 | 44 |
|  |  | 700B5-45 | 37 |
|  |  | 700B5-46 | 34 |
|  |  | 700B5-47 | 40 |
|  |  | 700B5-48 | 118 |
|  |  | 700B5-49 | 32 |
|  |  | 700B5-50 | 269 |

$\geq$100000 CPM = positive

The results presented in Table 5 show that barstar5 provides sufficient protection against the lethal effect of barnase to allow significantly more LUC positive shoots to regenerate. While only 15% of the shoots regenerating from wild type explants are LUC positive 46% of those regenerating from barstar5 explants are LUC positive. These data indicate that there is protection provided by the barstar5 line and that it is the lethal effect of the barnase gene that is leading to the reduced number of LUC positive shoots recovered with the pBH700 binary in wild type tobacco compared with the control binary, pBH710.

Example 4

This example is similar to example 2 except that the transformed plants are tomato plants instead of tobacco plants.

Tomato seeds (variety Baxters Early Bush Cherry) were sterilized and sewn onto TSRM media (MS salts, B5 vitamins, 30 g/L sucrose, pH 5.6 solidified with 0.2 g/L gelrite). The seeds were incubated at 28° C. under lights for 1 week after which the cotyledons were used as explants for transformation. A single explant was made from each cotyledon by excising it from the seedling near the stem and then removing its distal end. The explants were submerged in a solution of liquid TSRM (as above, but lacking the gelrite) which contained about 2×10$^7$ bacteria/ml.

After several minutes explants were transferred to plates containing TSRM medium supplemented with the following; 1 mg/l Zeatin, 1 mg/lIAA and 100 $\mu$M acetosyringone. Explants were cocultivated on this medium, overlayed with filter paper discs, at 24° C./dark for two days. Explants were then transferred to TSRM medium supplemented with the following; 1 mg/l Zeatin, 1 mg/lIAA, and 500 mg/l carbenecillin. The explants were cultured under the same conditions as the seeds for 3 days, and then were transferred to TSRM medium supplemented with the following; 1 mg/l Zeatin, 1 mg/lIAA, 500 mg/l carbenecillin, and 50 ug/L chlorsulfuron. The explants were returned to the same conditions as before and incubated until shoots formed.

To identify which shoots were transformed and which shoots had escaped the selection, 2 small segments of some of the leaves were removed and placed on a callusing medium consisting of TSRM medium supplemented with the following; 1 mg/l NAA, 0.1 mg/l 2,4-D, 0.1 mg/l BA, 500 mg/l carbenecillin, and 50 ug/L chlorsulfuron. Only the leaf pieces which formed callus were considered as transformed, while the pieces which did not form callus were considered as escapes. This analysis revealed that approximately 20% of the pBH700 shoots, 8% of the pBH710 shoots and 13% of the pNG5185 shoots on selection were not transformed.

TABLE 6

Relative Transformation Efficiency

|  | pNG5185 | pBH700 | pBH710 |
|---|---|---|---|
| # shoots on selection | 26 | 70 | 84 |
| # transformed shoots | 22 | 56 | 77 |
| explants selected | 20 | 100 | 100 |
| transformants/explant | 1.0 | 0.56 | 0.77 | pNG5185 = unmodified binary
pBH700 = active barnase-INT
pBH710 = barnase-INT deletion Each known transformant on the basis of the callus assay was assayed for luciferase activity by grinding up the entire leaf sample and attached callus as was done in example 2.

TABLE 7

Luciferase Activity

| xformant # | × 1000 CPM | xformant # | × 1000 CPM |
|---|---|---|---|
| 700-1 | 0 | 710-1 | 34 |
| 700-3 | 3 | 710-2 | 50000 |
| 700-5 | 14 | 710-3 | 41 |
| 700-6 | 15 | 710-4 | 14 |
| 700-7 | 15 | 710-5 | 50000 |
| 700-8 | 16 | 710-6 | 50000 |
| 700-9 | 15 | 710-7 | 50000 |
| 700-10 | 16 | 710-8 | 17 |
| 700-11 | 15 | 710-10 | 50000 |
| 700-13 | 22 | 710-11 | 50000 |
| 700-14 | 16 | 710-12 | 50000 |
| 700-15 | 1528 | 710-13 | 50000 |
| 700-16 | 13 | 710-14 | 58 |
| 700-17 | 7 | 710-15 | 94 |
| 700-20 | 24 | 710-16 | 48 |
| 700-22 | 14 | 710-17 | 128 |
| 700-23 | 16 | 710-18 | 102 |
| 700-24 | 15 | 710-19 | 50000 |
| 700-25 | 50000 | 710-20 | 50000 |
| 700-27 | 24 | 710-21 | 50000 |
| 760-28 | 17 | 710-22 | 50000 |
| 700-29 | 9 | 710-24 | 104 |
| 700-30 | 14 | 710-25 | 51 |
| 700-31 | 15 | 710-26 | 50000 |
| 700-32 | 15 | 710-27 | 50000 |
| 700-33 | 17 | 710-28 | 50000 |
| 700-35 | 13 | 710-29 | 50000 |
| 700-36 | 16 | 710-30 | 50000 |
| 700-37 | 11 | 710-31 | 50000 |
| 700-38 | 10 | 710-32 | 50000 |
| 700-39 | 18 | 710-33 | 50000 |
|  |  | 710-35 | 50000 |
|  |  | 710-36 | 50000 |
|  |  | 710-37 | 33 |
|  |  | 710-38 | 50000 |
|  |  | 710-39 | 24 |
|  |  | 710-41 | 24 |
|  |  | 710-42 | 50000 |
|  |  | 710-43 | 50000 |
|  |  | 710-44 | 50000 |
|  |  | 710-45 | 50000 |
|  |  | 710-46 | 15 |
|  |  | 710-47 | 50000 |
|  |  | 710-48 | 50000 |

TABLE 7-continued

| Luciferase Activity | | | |
|---|---|---|---|
| xformant # | × 1000 CPM | xformant # | × 1000 CPM |
| | | 710-49 | 2170 |
| | | 710-50 | 50000 |

The data presented in Tables 6 and 7 support the same conclusions in tomato as were made for tobacco in example 2, namely that the functional barnase-INT gene placed exterior to the T-DNA reduced the incidence of transfer of sequences beyond the left border, and that the barnase-INT construct had a nominal impact on the efficiency of transformation. A comparison of the tomato and tobacco data reveals a similarity. In terms of the frequency of integration of non-T-DNA sequences in control populations: 74% for tomato, 84% for tobacco, the reduction in transformation efficiency caused by inclusion of the barnase-INT gene external to the T-DNA: 27% for tomato, 30% for tobacco, and the efficiency of the barnase-INT gene strategy in reducing the frequency of integration of non-T-DNA sequences reflected in the low percentage of LUC+ transformants: 6% for tomato, 2% for tobacco. The data also indicate the high incidence of beyond the border transfer in the control population (84% LUC+). The data in Table 6 show that compared with the control binary (pBH710) the binary with the functional barnase-INT outside the T-DNA (pBH700) had only a 30% reduction in transformation efficiency. Comparing this binary with the non-modified binary (pNG5185) the reduction was less than three fold.

The above examples are provided to illustrate the invention, but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method for producing a transgenic plant containing a polynucleotide of interest, the method comprising:
   (a) introducing into a plurality of plant cells a T-DNA vector comprising:
      (i) a T-DNA sequence comprising a right border, a left border and the polynucleotide of interest positioned between the right border and left border, and
      (ii) a non-T-DNA sequence comprising a lethal polynucleotide sequence encoding a lethal polypeptide, wherein said non-T-DNA sequence is located beyond the left T-DNA border;
   (b) selecting a plant cell which comprises the T-DNA sequence and does not comprise the lethal polynucleotide sequence; and
   (c) regenerating a transgenic plant from the selected plant cell.

2. The method of claim 1, wherein the lethal polypeptide is a ribonuclease.

3. The method of claim 2, wherein the ribonuclease is Barnase.

4. The method of claim 3, wherein the Barnase has an intron in the coding region.

5. The method of claim 1, wherein the non-T-DNA sequence further comprises a screenable marker and the method further comprises detection of the screenable marker in the plant cells.

6. The method of claim 5, wherein the screenable marker encodes β-glucuronidase.

7. The method of claim 1, wherein the lethal polynucleotide sequence is within about 5 kb of the left border.

8. An isolated T-DNA vector comprising a T-DNA sequence comprising a right border and a left border and a non-T-DNA sequence comprising a lethal polynucleotide sequence encoding a lethal polypeptide, wherein said non-T-DNA sequence is located beyond the left T-DNA border.

9. The isolated T-DNA vector of claim 8, further comprising a polynucleotide of interest positioned between the right border and left border of the T-DNA sequence.

10. The isolated T-DNA vector of claim 8, further comprising a selectable marker positioned between the right border and left border of the T-DNA sequence.

11. The isolated T-DNA vector claim 8, wherein the lethal polypeptide is a ribonuclease.

12. The isolated T-DNA vector claim 11, wherein the ribonuclease is Barnase.

13. The isolated T-DNA vector claim 12, wherein the Barnase has an intron in the coding region.

14. The isolated T-DNA vector of claim 8, wherein the non-T-DNA sequence further comprises a screenable marker.

15. The isolated T-DNA vector of claim 14, wherein the screenabke marker encodes β-glucuronidase.

16. The isolated T-DNA vector of claim 8, wherein the lethal polynucleotide sequence is within 5 kb of the left border.

* * * * *